(12) United States Patent
Skillrud et al.

(10) Patent No.: US 11,738,188 B2
(45) Date of Patent: Aug. 29, 2023

(54) CONNECTION OF INTRAVASCULAR INTERVENTIONAL ELEMENTS AND ELONGATE MANIPULATION MEMBERS

(71) Applicant: Covidien LP, Mansfield, MA (US)

(72) Inventors: Erik Skillrud, Irvine, CA (US); Evan D. Epstein, Los Angeles, CA (US); Lily Chen, Irvine, CA (US); Chelsea L. Gregg, Irvine, CA (US); Daniel J. Deen, Long Beach, CA (US)

(73) Assignee: Covidien LP, Mansfield, MA (US)

( * ) Notice: Subject to any disclaimer, the term of this patent is extended or adjusted under 35 U.S.C. 154(b) by 620 days.

(21) Appl. No.: 16/946,146

(22) Filed: Jun. 8, 2020

(65) Prior Publication Data

US 2021/0379350 A1 Dec. 9, 2021

(51) Int. Cl.
*A61M 39/10* (2006.01)
*A61M 25/00* (2006.01)
(Continued)

(52) U.S. Cl.
CPC .......... *A61M 39/10* (2013.01); *A61M 25/007* (2013.01); *A61M 25/0021* (2013.01);
(Continued)

(58) Field of Classification Search
CPC .............. A61M 39/10; A61M 25/0021; A61M 25/007; A61M 25/0138; A61M 39/0247;
(Continued)

(56) References Cited

U.S. PATENT DOCUMENTS

| 777,777 A | 12/1904 | Carlson et al. |
| 4,781,177 A | 11/1988 | Lebigot |

(Continued)

FOREIGN PATENT DOCUMENTS

| CN | 108042176 A | 5/2018 |
| EP | 1832250 A1 | 9/2007 |

(Continued)

OTHER PUBLICATIONS

Extended European Search Report dated Oct. 8, 2021, European Patent Application No. 21175555.8, 7 pages.

*Primary Examiner* — James D Ponton
(74) *Attorney, Agent, or Firm* — FORTEM IP LLP

(57) ABSTRACT

A device for intravascular intervention can comprise an interventional element, an elongate manipulation member having a retention portion, and a joining element. The elongate element can comprise a distally located attachment portion. The interventional element includes a proximal end portion with a hole therethrough, the attachment portion of the elongate member extending through the hole at the bend such that first and second segments of the elongate member each extend proximally from the hole. A retention portion includes an arm extends proximally of the hole and a shoulder protruding radially outwardly from a proximal portion of the arm. A joining element circumferentially surrounds at least a portion of the retention portion and at least a portion of the first and second segments of the elongate member such that a proximal end of the joining element is positioned distal to the shoulder of the retention portion.

20 Claims, 8 Drawing Sheets

(51) Int. Cl.
*A61M 25/01* (2006.01)
*A61M 39/02* (2006.01)

(52) U.S. Cl.
CPC .... *A61M 25/0138* (2013.01); *A61M 39/0247* (2013.01); *A61M 2025/0042* (2013.01); *A61M 2039/0258* (2013.01)

(58) Field of Classification Search
CPC .. A61M 2025/0042; A61M 2039/0258; A61B 2017/2215; A61B 17/221; A61B 17/22031; A61B 2017/22035
See application file for complete search history.

(56) References Cited

U.S. PATENT DOCUMENTS

| | | |
|---|---|---|
| 4,832,055 A | 5/1989 | Palestrant |
| 5,190,058 A | 3/1993 | Jones et al. |
| 5,250,071 A | 10/1993 | Palermo |
| 5,261,916 A | 11/1993 | Engelson |
| 5,312,416 A | 5/1994 | Spaeth et al. |
| 5,364,357 A | 11/1994 | Aase |
| 5,370,657 A | 12/1994 | Irie |
| 5,601,600 A | 2/1997 | Ton |
| 5,643,277 A | 7/1997 | Soehendra et al. |
| 5,743,905 A | 4/1998 | Eder et al. |
| 5,941,895 A | 8/1999 | Myler et al. |
| 5,944,733 A | 8/1999 | Engelson |
| 6,027,508 A | 2/2000 | Ren et al. |
| 6,059,719 A * | 5/2000 | Yamamoto ....... A61B 17/00234 606/1 |
| 6,099,546 A | 8/2000 | Gia |
| 6,110,483 A | 8/2000 | Whitbourne et al. |
| 6,159,219 A | 12/2000 | Ren |
| 6,187,016 B1 | 2/2001 | Hedges et al. |
| 6,416,505 B1 | 7/2002 | Fleischman et al. |
| 6,506,205 B2 | 1/2003 | Goldberg et al. |
| 6,569,181 B1 | 5/2003 | Burns |
| 6,821,291 B2 | 11/2004 | Bolea et al. |
| 6,835,185 B2 | 12/2004 | Ramzipoor et al. |
| 6,997,937 B2 | 2/2006 | Jacobsen et al. |
| 7,074,197 B2 | 7/2006 | Reynolds et al. |
| 7,083,567 B2 | 8/2006 | Mawad |
| 7,105,019 B2 | 9/2006 | Hojeibane |
| 7,169,154 B1 | 1/2007 | Que et al. |
| 7,258,696 B2 | 8/2007 | Rabkin et al. |
| 7,329,269 B2 | 2/2008 | Shapiro et al. |
| 7,611,525 B2 | 11/2009 | Baig |
| 7,686,846 B2 | 3/2010 | Laborde et al. |
| 7,771,463 B2 | 8/2010 | Ton et al. |
| 7,789,915 B2 | 9/2010 | Lavelle et al. |
| 7,967,838 B2 | 6/2011 | Chanduszko et al. |
| 8,043,322 B2 | 10/2011 | Hendriksen et al. |
| 8,052,713 B2 | 11/2011 | Khosravi et al. |
| 8,105,349 B2 | 1/2012 | Hendriksen et al. |
| 8,137,292 B2 | 3/2012 | Skujins et al. |
| 8,182,529 B2 | 5/2012 | Gordon et al. |
| 8,202,292 B2 | 6/2012 | Kelleii |
| 8,222,566 B2 | 7/2012 | Shireman et al. |
| 8,328,860 B2 | 12/2012 | Strauss et al. |
| 9,358,021 B2 | 6/2016 | Losordo et al. |
| 10,098,657 B2 | 10/2018 | Losordo et al. |
| 10,111,682 B2 | 10/2018 | Johnson et al. |
| 10,835,282 B2 | 11/2020 | Johnson et al. |
| 2002/0010487 A1 | 1/2002 | Evans et al. |
| 2002/0022858 A1 | 2/2002 | Demond et al. |
| 2002/0069527 A1 | 6/2002 | Tsuda et al. |
| 2002/0099437 A1 | 7/2002 | Anson et al. |
| 2002/0103501 A1 | 8/2002 | Diaz et al. |
| 2003/0004538 A1 | 1/2003 | Secrest et al. |
| 2003/0078519 A1 | 4/2003 | Salahieh et al. |
| 2004/0186510 A1 | 9/2004 | Weaver |
| 2004/0220655 A1 | 11/2004 | Swanson et al. |
| 2005/0119673 A1 | 6/2005 | Gordon et al. |
| 2005/0165441 A1 | 7/2005 | McGuckin et al. |
| 2007/0055299 A1 | 3/2007 | Ishimaru et al. |
| 2007/0233175 A1 | 10/2007 | Zaver et al. |
| 2008/0306504 A1 | 12/2008 | Win et al. |
| 2009/0082800 A1 | 3/2009 | Janardhan |
| 2009/0125053 A1 | 5/2009 | Ferrera et al. |
| 2009/0326636 A1 | 12/2009 | Hashimoto et al. |
| 2010/0094395 A1 | 4/2010 | Kelleii |
| 2010/0249911 A1 | 9/2010 | Alkhatib |
| 2011/0054519 A1 | 3/2011 | Neuss |
| 2011/0060212 A1 | 3/2011 | Slee et al. |
| 2011/0160763 A1 | 6/2011 | Ferrera et al. |
| 2011/0178366 A1 | 7/2011 | Suzuki et al. |
| 2011/0184452 A1 | 7/2011 | Huynh et al. |
| 2011/0190797 A1 | 8/2011 | Fulkerson et al. |
| 2011/0264194 A1 | 10/2011 | Griswold |
| 2012/0022633 A1 | 1/2012 | Olson et al. |
| 2012/0041472 A1 | 2/2012 | Tan et al. |
| 2012/0071987 A1 | 3/2012 | Levy |
| 2012/0209310 A1 | 8/2012 | Chen et al. |
| 2012/0259354 A1 | 10/2012 | Kellett |
| 2014/0194911 A1 | 7/2014 | Johnson et al. |
| 2015/0328438 A1 * | 11/2015 | Baid ................ A61M 25/0618 604/164.08 |
| 2016/0354106 A1 | 12/2016 | Losordo et al. |
| 2018/0325532 A1 * | 11/2018 | Skillrud ............ A61B 17/221 |
| 2021/0007769 A1 | 1/2021 | Johnson et al. |

FOREIGN PATENT DOCUMENTS

| | | |
|---|---|---|
| EP | 3593742 A1 | 1/2020 |
| JP | 2012505040 A | 3/2012 |
| WO | 0207650 A1 | 1/2002 |
| WO | 2007054307 A2 | 5/2007 |

\* cited by examiner

CONNECTION OF INTRAVASCULAR INTERVENTIONAL ELEMENTS AND ELONGATE MANIPULATION MEMBERS

TECHNICAL FIELD

The present technology relates generally to devices and methods for connecting intravascular interventional elements to elongate manipulation members.

BACKGROUND

A variety of procedures can be performed by manipulating an intravascular interventional element connected to a manipulation member, such as, for example, a wire or hypotube. In some instances, interventional elements can be manipulated by a practitioner from a location outside the body using the manipulation member. Thus, the manipulation member may extend from a location outside the body to a treatment location within the body. The manipulation member may extend through a catheter from the location outside the body to the treatment location. Intravascular interventional elements can be connected to manipulation members in a variety of ways.

SUMMARY

The present technology is illustrated, for example, according to various aspects described below. Various examples of aspects of the present technology are described as numbered clauses (1, 2, 3, etc.) for convenience. These are provided as examples and do not limit the present technology. It is noted that any of the dependent clauses may be combined in any combination, and placed into a respective independent clause. The other clauses can be presented in a similar manner.

Clause 1. A device for intravascular intervention, the device comprising:
  an elongate manipulation member comprising a distally located attachment portion, the attachment portion comprising a first segment, a second segment, and a bend between the first and second segments;
  an interventional element comprising:
    a proximal end portion including a hole therethrough, the attachment portion of the elongate member extending through the hole at the bend such that the first and second segments each extend proximally from the hole; and
    a retention portion comprising an arm extending proximally of the hole and a shoulder protruding radially outwardly from a proximal portion of the arm; and
  a joining element configured to circumferentially surround at least a portion of the retention portion and at least a portion of the first and second segments of the elongate member such that a proximal end of the joining element is positioned distal to the shoulder of the retention portion.

Clause 2. The device of any one of the Clauses herein, wherein the arm is a first arm and the shoulder is a first shoulder, the retention portion further comprising:
  a second arm extending proximally of the hole; and
  a second shoulder protruding radially outwardly from a proximal portion of the second arm,
  wherein the joining element is configured to circumferentially surround at least a portion of the retention portion such that the proximal end of the joining element is positioned distal to the second shoulder of the retention portion.

Clause 3. The device of any one of the Clauses herein, further comprising a longitudinal axis intersecting the hole, wherein the first arm extends away from the longitudinal axis in a first direction, and wherein the second arm extends away from the longitudinal axis in a second direction opposite the first.

Clause 4. The device of any one of the Clauses herein, further comprising a third shoulder protruding radially outwardly from the first arm at a position distal to the first shoulder; and a fourth shoulder protruding radially outwardly from the second arm at a position distal to the second shoulder.

Clause 5. The device of any one of the Clauses herein, wherein the third shoulder and the fourth shoulder are configured to engage a distal end of the joining element.

Clause 6. The device of any one of the Clauses herein, wherein the shoulder comprises a substantially planar distal-facing surface and an angled proximal-facing surface, the distal-facing surface configured to engage the proximal end of the joining element.

Clause 7. The device of any one of the Clauses herein, wherein the joining element comprises cylindrical band.

Clause 8. The device of any one of the Clauses herein, wherein each of the first and second segments of the elongate member extends proximally of the band.

Clause 9. The device of any one of the Clauses herein, wherein the arm is radially outwardly biased, and wherein the joining element is configured to retain the arm in a displaced state.

Clause 10. The device of any one of the Clauses herein, wherein the shoulder protrudes laterally to an extent, measured from the arm, by an amount that is greater than or equal to a wall thickness the joining element.

Clause 11. The device of any one of the Clauses herein, wherein:
  the proximal end portion of the interventional element has a top side and a bottom side;
  the hole extends through the proximal end portion between the top side and the bottom side;
  at least one of the first segment or the second segment of the elongate member has an extending portion that extends into a region that is (i) between the top side and the bottom side of the proximal end portion, and (ii) between the shoulder of the retention portion and the hole.

Clause 12. A device for intravascular intervention, the device comprising:
  a band having a lumen;
  an elongate manipulation member having a distally located attachment portion, the manipulation member extending through the lumen; and
  an interventional element comprising:
    a proximal end portion including a hole therethrough, the attachment portion of the elongate member extending through the hole; and
    a plurality of projections extending proximally of the hole and through the lumen, at least one of the projections including a flange extending laterally away from a longitudinal axis of the device and configured to engage with the band.

Clause 13. The device of any one of the Clauses herein, wherein the flange is configured to abut a proximal end portion of the band.

Clause 14. The device of any one of the Clauses herein, wherein the at least one projection comprises a proximally facing surface opposite the flange, the proximally facing surface being sloped in the proximal direction towards a central longitudinal axis of the device.

Clause 15. The device of any one of the Clauses herein, wherein the plurality of projections are biased laterally outwardly from a central longitudinal axis of the device.

Clause 16. The device of any one of the Clauses herein, wherein the flange limits distal movement of the interventional element with respect to the band.

Clause 17. A device for intravascular intervention, the device comprising:
an elongate manipulation member comprising a distally located attachment portion;
an interventional element comprising:
a proximal end portion including a hole therethrough, the attachment portion of the elongate member extending through the hole; and
a plurality of arms extending proximally of the hole and extending laterally outwardly from a longitudinal axis of the device, each of the arms having a protrusion thereon having a proximal-facing surface and a distal-facing surface; and
a joining element circumferentially surrounding the arms such that each of the distal-facing surfaces of the protrusions abuts a proximal-facing engagement surface of the joining element.

Clause 18. The device of any one of the Clauses herein, wherein the distal-facing engagement surface of the joining element comprises a proximal end face of the joining element.

Clause 19. The device of any one of the Clauses herein, wherein the distal-facing surfaces of the protrusions are sloped laterally inwardly in the proximal direction.

Clause 20. The device of any one of the Clauses herein, wherein a portion of the elongate manipulation member extends laterally between the arms.

Clause 21. A device for intravascular intervention, the device comprising:
an elongate manipulation member comprising a distally located attachment portion, the attachment portion comprising a first segment, a second segment, and a bend between the first and second segments;
an intervention element comprising:
a proximal end portion including a hole therethrough, the attachment portion of the elongate member extending through the hole at the bend such that the first and second segments each extend proximally from the hole; and
a plurality of protrusions extending proximally from the proximal end portion, each of the protrusions having a first end at the proximal end portion and a second end, wherein
at least one of the protrusions includes a flange extending radially outwardly from a longitudinal axis of the device; and,
each of the protrusions have (a) a first configuration in which the second ends are separated from the longitudinal axis of the device by a first radial distance, and (b) a second configuration in which the second ends are separated from the longitudinal axis of the device by a second radial distance that is less than the first radial distance, wherein the first and second radial distances are measured as a dimension generally orthogonal to the longitudinal axis of the device a joining element having a lumen therethrough, wherein the first and second segments are positioned within the lumen, and the protrusions are positioned within the lumen such that the protrusions assume the second configuration.

Clause 22. The device of any one of the Clauses herein, wherein the flange abuts a surface of the joining element.

Clause 23. The device of any one of the Clauses herein, wherein the flange prevents proximal and/or distal translation of the joining element relative to the flange.

Clause 24. The device of any one of the Clauses herein, wherein the joining element prevents proximal and/or distal translation of the first and second segments relative to the hole.

Clause 25. The device of any one of the Clauses herein, wherein the proximal end portion has a top side and a bottom side, wherein the first segment is on the top side, the second segment is on the bottom side, and in the second configuration, the protrusions lie between the first and second segments, and the plurality of protrusions provides stiffness to the attachment portion of the elongate manipulation member.

Clause 26. A device for intravascular intervention, the device comprising:
an elongate manipulation member comprising a distally located attachment portion, the attachment portion comprising a first segment, a second segment, and a bend between the first and second segments:
an intervention element comprising:
a proximal end portion including a hole therethrough, the attachment portion of the elongate member extending through the hole at the bend such that the first and second segments each extend proximally from the hole; and
a plurality of protrusions extending proximally from the proximal end portion and extending radially outwardly from a longitudinal axis of the device; and
a joining element having a lumen therethrough, wherein the joining element is positioned to circumferentially surround the protrusions such that the protrusions apply a force to the joining element that prevents the joining element from translating relative to the elongate manipulation member.

Additional features and advantages of the present technology are described below, and in part will be apparent from the description, or may be learned by practice of the present technology. The advantages of the present technology will be realized and attained by the structure particularly pointed out in the written description and claims hereof as well as the appended drawings.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present disclosure.

DETAILED DESCRIPTION

I. Example Intravascular Intervention Devices

In the following detailed description, specific details are set forth to provide an understanding of the subject technology. It will be apparent, however, to one ordinarily skilled in the art that the subject technology may be practiced without some of these specific details. In other instances, well-known structures and techniques have not been shown in detail so as not to obscure the subject technology.

The present technology provides devices, systems, and methods for removing clot material from a blood vessel lumen. Although many of the embodiments are described below with respect to devices, systems, and methods for treating a cerebral or intracranial embolism, other applications and other embodiments in addition to those described herein are within the scope of the technology. For example, the treatment systems and methods of the present technology may be used to remove emboli from body lumens other than blood vessels (e.g., the digestive tract, etc.) and/or may be used to remove emboli from blood vessels outside of the brain (e.g., pulmonary, abdominal, cervical, or thoracic blood vessels, or peripheral blood vessels including those within the legs or arms, etc.). In addition, the treatment systems and methods of the present technology may be used to remove luminal obstructions other than clot material (e.g., plaque, resected tissue, foreign material, etc.).

Figure 1A:
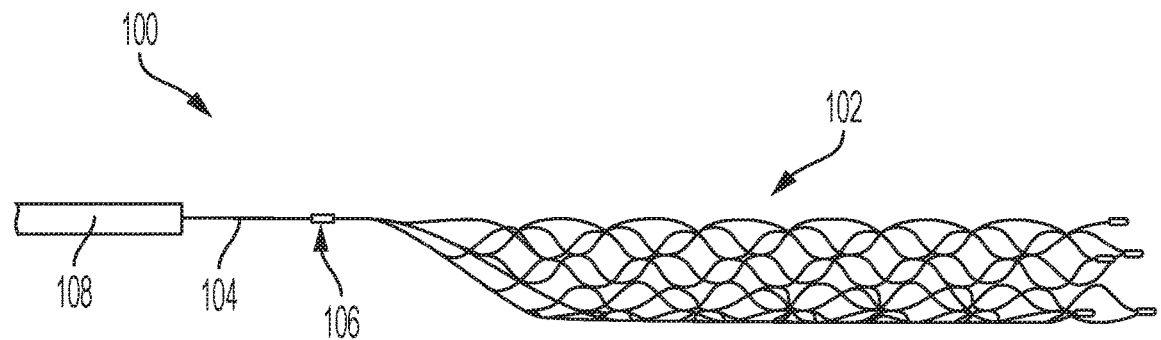
FIG. 1A is a schematic illustration of an example device for intravascular intervention according to some embodiments.

FIG. 1A is a schematic illustration of an example medical device 100 for intravascular intervention, according to some embodiments. The device 100 illustrated in FIG. 1A comprises an interventional element 102 and a manipulation member 104 joined at a connection 106. The device 100 is illustrated as extending out of a distal end of a catheter 108.

The interventional element 102 can comprise an element for performing an intravascular intervention, for example a stent-like device or other type of interventional elements. The interventional element 102 can comprise a device configured for various purposes, such as, for example, aneurysm bridging or treatment of ischemic stroke. In various embodiments, the interventional element 102 can take any number of forms, for example a removal device, a thrombectomy device, or other suitable medical device. For example, in some embodiments the interventional element 102 may be a stent and/or stent retriever, such as Medtronic's Solitaire™ Revascularization Device, Stryker Neurovascular's Trev® ProVue™ Stentriever, or other suitable devices. In some embodiments, the interventional element 102 may be a coiled wire, a weave, and/or a braid formed of a plurality of braided filaments. Examples of suitable interventional element 102 include any of those disclosed in U.S. Pat. No. 7,300,458, filed Nov. 5, 2007, U.S. Pat. No. 8,940,003, filed Nov. 22, 2010, U.S. Pat. No. 9,039,749, filed Oct. 1, 2010, and U.S. Pat. No. 8,066,757, filed Dec. 28, 2010, each of which is incorporated by reference herein in its entirety.

The manipulation member 104 can be any suitable elongate member configured to advance the interventional element 102 to a treatment site within a blood vessel. For example, the manipulation member 104 can be or include a wire, tube (e.g., a hypotube), coil, or any combination thereof. The manipulation member 104 can have a length sufficient to extend from a location outside the patient's body through the vasculature to a treatment site within the patient's body. The manipulation member 104 can be monolithic or formed of multiple joined segments, in some embodiments. In some embodiments, the manipulation member 104 can include a laser-cut hypotube having a spiral cut pattern (or other pattern of cut voids) formed in its sidewall along at least a portion of its length. The manipulation member 104 can comprise or consist of nickel titanium alloy, stainless steel, or other metals or alloys, or any polymer, suited for intracorporeal use. In embodiments that comprise multiple joined segments, the segments may be of the same or different materials. For example, some or all of the manipulation member 104 can be formed of stainless steel, or other suitable materials known to those skilled in the art. Nickel titanium alloy may be preferable for kink resistance and reduction of imaging artifacts.

The catheter 108 can be configured to access relatively distal locations in a patient including, for example, the middle cerebral artery (MCA), internal carotid artery (ICA), the Circle of Willis, and tissue sites more distal than the MCA, ICA, and the Circle of Willis. The MCA, as well as other vasculature in the brain or other relatively distal tissue sites (e.g., relative to the vascular access point), may be relatively difficult to reach with a catheter, due at least in part to the tortuous pathway (e.g., comprising relatively sharp twists or turns) through the vasculature to reach these tissue sites. As such, the catheter may be structurally configured to be relatively flexible, pushable, and relatively kink- and buckle-resistant, so that it may resist buckling when a pushing force is applied to a relatively proximal section of the catheter to advance the catheter distally through vasculature, and so that it may resist kinking when traversing around a tight turn in the vasculature. In some examples, the catheter 108 is configured to substantially conform to the curvature of the vasculature. In addition, in some examples, the catheter 108 has a column strength and flexibility that allow at least distal portion of the catheter to be navigated from a femoral artery, through the aorta of the patient, and into the intracranial vascular system of the patient, e.g., to reach a relatively distal treatment site.

Although primarily described as being used to reach relatively distal vasculature sites, the catheter 108 may also be configured to be used with other target tissue sites. For example, the catheter 108 may be used to access tissue sites throughout the coronary and peripheral vasculature, the gastrointestinal tract, the urethra, ureters, fallopian tubes, veins and other body lumens.

According to some embodiments, the catheter 108 can be formed as a generally tubular member extending along and about a central axis. According to some embodiments, the microcatheter 108 can be generally constructed to track over a conventional guidewire in the cervical anatomy and into the cerebral vessels associated with the brain and may also be chosen according to several standard designs that are generally available. Accordingly, the catheter 108 can have a length that is at least 125 cm long, and more particularly may be between about 125 cm and about 175 cm long. In some embodiments, the catheter can have a lumen diameter of less than about 0.03", such as about 0.017", 0.021", or 0.027" lumen diameter. Other designs and dimensions are contemplated.

During advancement, the interventional element 102 can be removably disposed within the catheter 108 in a low-profile or constrained configuration. Once the catheter 108 is in positioned such that its distal end is adjacent a treatment site (e.g., a site of a blood clot within the vessel), the interventional element 102 can be released from the catheter 108 (e.g., via proximal retraction of the catheter 108), and the interventional element 102 may be released into its expanded state.

According to some embodiments, the body of the catheter 108 can be made from various thermoplastics, e.g., polytetrafluoroethylene (PTFE or TEFLON®), fluorinated ethylene propylene (FEP), high-density polyethylene (HDPE), polyether ether ketone (PEEK), etc., which can optionally be lined on the inner surface of the catheter or an adjacent surface with a hydrophilic material such as polyvinylpyrrolidone (PVP) or some other plastic coating. Additionally, either surface can be coated with various combinations of different materials, depending upon the desired results.

The interventional element 102 and the manipulation member 104 can be substantially permanently attached together at the connection 106. That is, the interventional element 102 and the manipulation member 104 can be attached together in a manner that, under the expected use conditions of the device 100, the interventional element and the manipulation member would not become unintentionally separated from one another. In some embodiments, the device 100 can comprise a portion, located proximally or distally of the connection 106, that is configured for selective detachment of the interventional element 102 from the manipulation member 104. For example, such a portion can comprise an electrolytically severable segment of the manipulation member. In some embodiments, the device 100 can be devoid of any feature that would permit selective detachment of the interventional element 102 from the manipulation member 104. As described in more detail elsewhere herein, in some embodiments the connection 106 can provide a mechanical interlock between the interventional element 102 and the manipulation member 104.

Figure 1B:
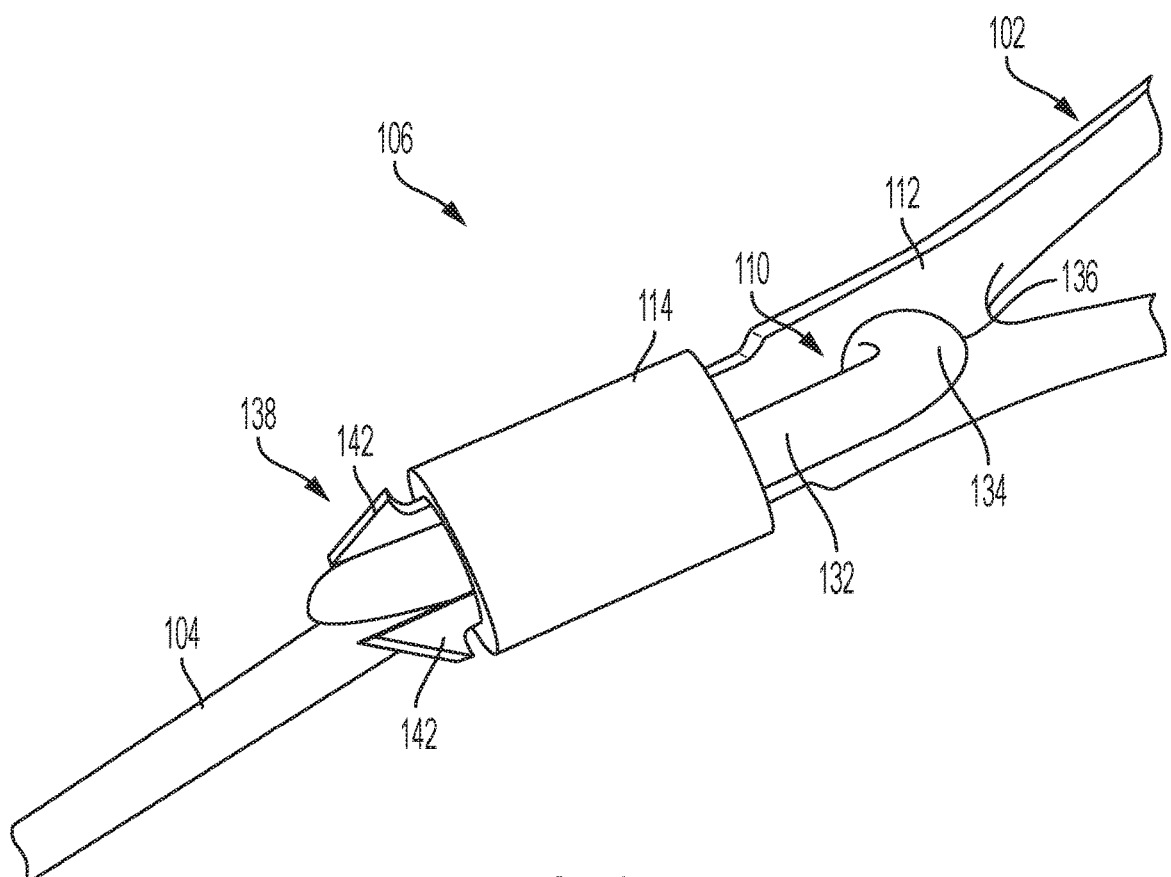
FIG. 1B is an enlarged perspective view of the connection between the manipulation member and the interventional element shown in FIG. 1A.
Figure 2:
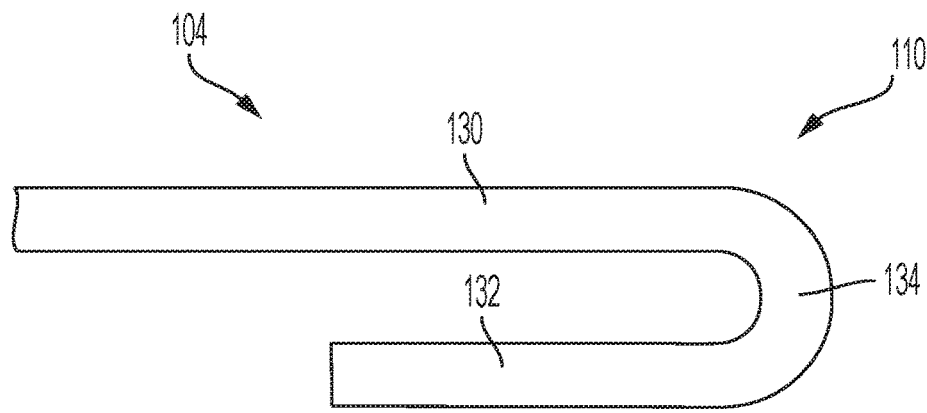
FIG. 2 is a schematic side view of an attachment portion of a manipulation member according to some embodiments.
Figure 3A:
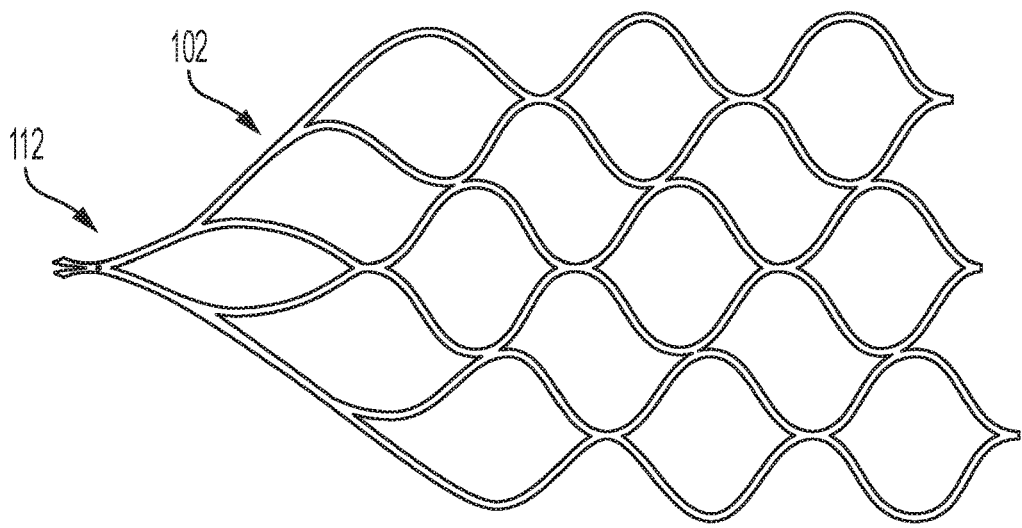
FIG. 3A is a plan view of an interventional element in an unfurled configuration according to some embodiments.
Figure 3B:
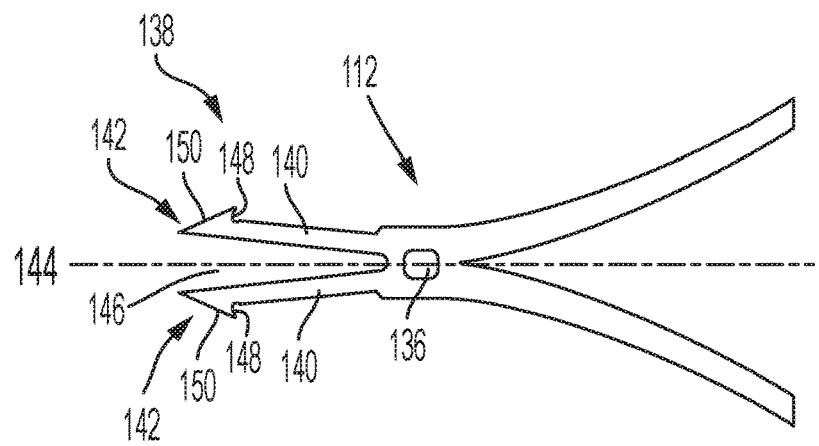
FIG. 3B is an enlarged view of a proximal portion of the interventional element shown in FIG. 3A.
Figure 4A:
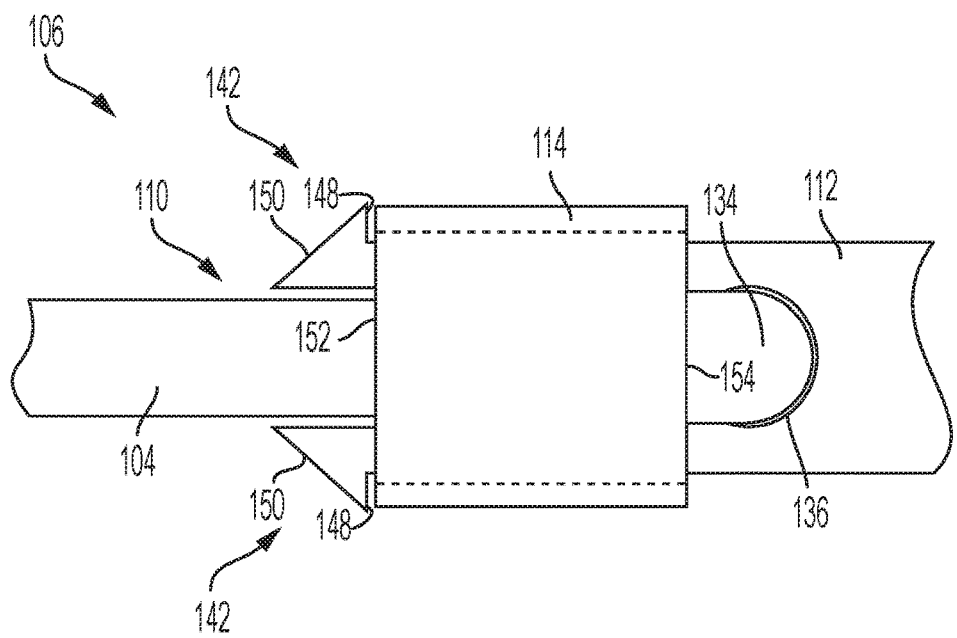
FIG. 4A is a schematic top view of a connection between a manipulation member and an interventional element according to some embodiments.
Figure 4B:
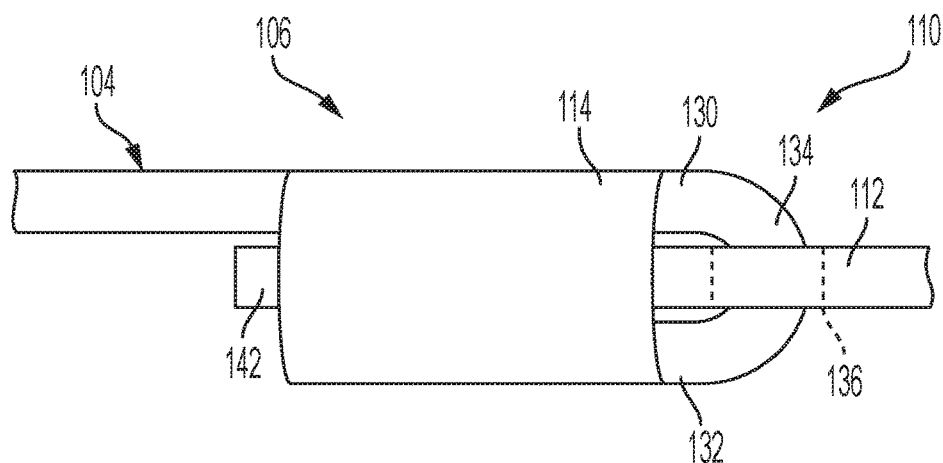
FIG. 4B is a schematic side view of the connection shown in FIG. 4A.
Figure 4C:
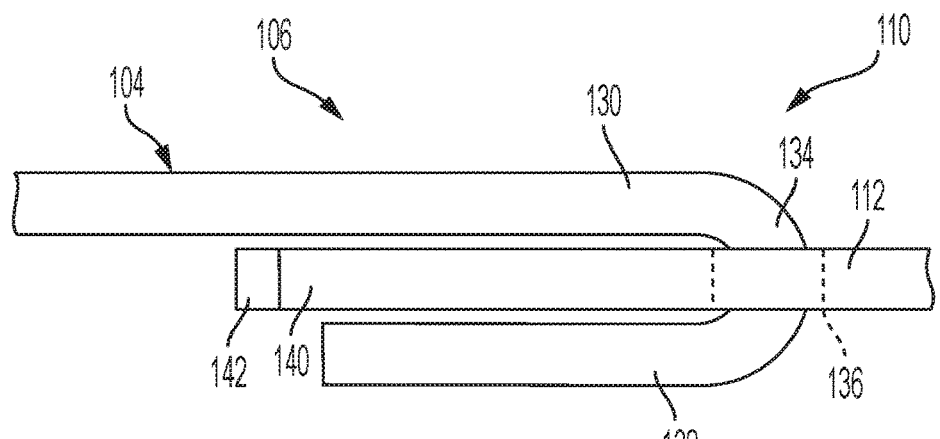
FIG. 4C is a schematic side view of the connection shown in FIGS. 4A and 4B, with the joining element omitted for clarity.

FIG. 1B illustrates an enlarged perspective view of the connection 106, according to some embodiments, between the manipulation member 104 and the interventional element 102. FIG. 2 illustrates a schematic top view of the attachment portion 110 of the manipulation member 104. FIG. 3A illustrates a plan view of an interventional element 102 including a proximal end portion 112, and FIG. 3B illustrates an enlarged detail view of the proximal end portion 112 of the interventional element 102. FIGS. 4A and 4B illustrate schematic top and side views, respectively, of the connection 106 between the manipulation member 104 and the interventional element 102, including a joining element 114. FIG. 4C illustrates a schematic side view of the connection 106 with the joining element 114 omitted for clarity.

With reference to FIGS. 1A-4C together, the connection 106 can comprise an attachment portion 110 of the manipulation member 104. The attachment portion 110 can extend through a hole 136 disposed in a proximal portion 112 of the interventional element 102. A joining element 114 (e.g., a band, sleeve, collar, clip, coil or other suitable structure) can at least partially circumferentially surround at least a portion of the proximal portion 112 of the interventional element 102. A plurality of engagement members 142 disposed on a retention portion 138 of the interventional element 102 can be positioned proximal of the joining element 114 and configured to engage the joining element 114 to retain the interventional element 102 with respect to the manipulation member 104, as described in more detail herein.

The connection 106 can be dimensioned to fit through a catheter (e.g., catheter 108) for delivery to a treatment location within the body of a patient. In some embodiments, the connection 106 can be dimensioned fit through a microcatheter suitable for delivery into the neurovasculature. For example, the microcatheter can have an inner diameter of about 0.027 inch or less, about 0.021 inch or less, or about 0.017 inch or less.

In some embodiments, the manipulation member 104 can taper between a proximal end and a distal end, for example having a larger diameter at the proximal end than at the distal end. The manipulation member 104 can taper continuously or in spaced increments or discrete locations along all or a portion of its length. Any tapering portion of the manipulation member 104 can taper at a constant rate or at a variable rate per unit length. The attachment portion 110 can taper from a diameter of approximately 0.0065 inch, at a location just proximal to the connection 106, to approximately 0.0045 inch, at the terminal and the manipulation member 104. In some embodiments, manipulation member 104 can have a diameter of approximately 0.007 inch along the attachment portion 110.

As best seen in FIG. 2, the attachment portion 110 can comprise a first segment 130, the second segment 132, and a bend 134 between the first and second segments. In some embodiments, the attachment portion 110 can form a hook or u-shaped element. One or both of the first segment 130 and the second segment 132 can be substantially straight or curved. In some embodiments, the first segment 130 and the second segment 132 can be generally parallel to each other away from the bend 134. As illustrated, a distal terminal end of the manipulation member 104 can be located proximal of the bend 134 in the device manipulation member 104. In some embodiments, the attachment portion 110 can comprise a bend of approximately 180°.

In some embodiments, manipulation member 104 can have a nominal diameter of 0.0055 inch at the bend 134 of the attachment portion 110. In some embodiments, the manipulation member 104 has a circular cross-section prior to being bent, and an ovoid cross-section after being bent. In some embodiments, the bend 134 can have a radius that is less than double a maximum cross-sectional dimension, e.g., diameter, of the manipulation member 104 in the bend. In some embodiments, the bend 134 can have a radius that is less than a maximum cross-sectional dimension, e.g., diameter, of the manipulation member 104 in the bend. In some embodiments, the bend radius can vary through the bend.

The attachment portion 110 can have a maximum lateral dimension that is measured in a direction perpendicular to a longitudinal axis, extending in a proximal-distal direction, of the device 100. In some embodiments, the maximum lateral dimension is less than 0.027 inch, less than 0.021 inch, or less than 0.015 inch. In some embodiments, the maximum lateral dimension is less than 0.07 mm, less than 0.05 mm, or less than 0.04 mm. In some embodiments, the maximum lateral dimension is less than four times a maximum cross-sectional dimension, e.g., diameter, of the manipulation member 104 along the attachment portion 110. In some embodiments, the maximum lateral dimension is less than 0.07 mm, less than 0.05 mm, or less than 0.04 mm. In some embodiments, the maximum lateral dimension is less than three times a maximum cross-sectional dimension, e.g., diameter, of the manipulation member 104 along the attachment portion 110.

FIG. 3A is a plan view of an interventional element 102, depicted in an unfurled or flattened configuration for ease of understanding, and FIG. 3B is an enlarged detail view of the proximal portion 112 of the interventional element 102. The proximal portion 112 can be formed of any of nickel titanium alloy, stainless steel, or other materials suitable for introduction into the body for intravascular intervention. The proximal portion 112 can be configured such that the attachment portion 110 of the manipulation member 104 can extend around a part of the proximal portion 112. For example, the proximal portion 112 can comprise an opening 136, such as a hole, slot, window, or aperture, therethrough.

The opening 136 shown in FIG. 3B can be sized and shaped to permit the bend 134 of the attachment portion 110 to extend therethrough. For example, the opening 136 can be slightly larger than the cross-section of the attachment portion 110 that extends through the hole. The opening 136 can be ovoid, for example. The hole or slot can be located proximate a proximal terminal end of the interventional element 102.

The proximal portion 112 of the interventional element 102 can comprise a retention portion 138 positioned proximally of the opening 136. The retention portion 138 can include one or more projections or arms 140 extending proximally of the opening 136. In some embodiments, each arm 140 can include an engagement member 142, for example a protrusion, flange, bump, ridge, shoulder, barb, or other suitable structural feature. In some embodiments, the engagement member 142 extends radially or laterally outwardly away from the arm 140 and/or away from a central longitudinal axis of the device 100. The engagement member 142 can be positioned at a proximal portion (e.g., at or near a proximal terminus) of its arm 140. In some embodiments, the engagement member 142 can be positioned at other locations with respect to the arm 140. In some embodiments, the proximal portion 112 of the interventional element 102, including the retention portion 138 can have a substantially constant thickness, such as would result from the interventional element 102 being cut from a tube or sheet of material, for example. In other embodiments, the thickness of the proximal portion 112 can vary across its length, width, or both.

The arms 140 can optionally be configured such that the lateral or radial distance between their outer edges is slightly larger than an inner diameter or inner width of the joining element 114. In such embodiments, the arms 140 maintain a residual spring tension or outward pre-load or bias when the joining element 114 is in place on the arms. This is because the joining element 114 prevents the arms from moving laterally outward to the rest or unbiased position that they would otherwise occupy. The resulting residual tension increases the stability of the connection and maintains the joining element in position on the arms 140.

In the illustrated embodiment, the retention portion 138 includes two arms 140 arranged symmetrically with respect to a central longitudinal axis 144 and spaced apart from one another laterally to define a region 146. In various embodiments, the number of arms 140 can vary. For example, the retention portion 138 can include a single arm 140, or three, four, five, six, or more arms 140. Similarly, only some of the arms 140 may include an engagement member 142, or all of the arms 140 may include an engagement member 142.

The engagement members 142 of the retention portion 138 can each comprise a distal-facing surface 148 and a proximal-facing surface 150. In some embodiments, the distal-facing surface 148 forms a shoulder, planar surface, flange, or other suitable engagement surface that is configured to abut or otherwise engage with a corresponding engagement surface of the joining element 114. The For example, as seen in FIG. 4A, the distal-facing surface 148 can be positioned to abut the proximal end face 152 of the joining element 114. In some embodiments, the distal-facing surface 148 can extend radially outwardly away from the arm 140, for example extending laterally to an extent, measured from the arm 140, that is greater than a wall thickness of the joining element 114. In some embodiments, the distal-facing surface 148 forms an oblique angle with the longitudinal axis of the device 100, for example being substantially orthogonal to the longitudinal axis of the device 100.

In some embodiments, the proximal-facing surface 150 of the engagement member 142 can be sloped, for example being sloped radially inwardly in the proximal direction. In this orientation, the engagement members 142 can facilitate slidable engagement with the joining element 114 to achieve mechanical interlock. For example, with the manipulation member 104 positioned such that the attachment portion 110 extends through the hole 136 in the interventional element 102, the joining element 114 can be first positioned proximal to the interventional element 102, with the manipulation member 104 extending through a lumen of the joining element 114. As the joining element is slidably advanced in a distal direction, a distal end face 154 of the joining element may contact the proximal-facing surfaces 150 of the engagement members 142. Due to the sloped surfaces of the proximal-facing surfaces 150, the engagement members 142 and the arms 140 can be urged radially inwardly, into a flexed or bowed configuration. In this state, the combined lateral dimension of the engagement members 142 can be less than a lumen diameter of the joining element 114, such that the joining element 114 can be slidably advanced in a distal direction over the engagement members 142. Once the proximal end face 152 of the joining element 114 has moved distally beyond the distal-facing surfaces 148 of the engagement members 142, the engagement members 142 may be at least partially released from the radially constrained state (e.g., the arms 140 may move radially outwardly) to achieve the interlocked configuration shown in FIG. 4A. Once in this interlocked configuration, distal movement of the interventional element 102 is limited by engagement between the distal-facing surfaces 148 and the joining element 114.

In some embodiments, the arms 140 can be configured such that they do not underlie the attachment portion 110 of the manipulation member 104 in the device 100. For example, the arms 140 do not extend into the region 146. In some embodiments, when the attachment portion 110 of the manipulation member 104 is mated with the proximal end portion 112 of the interventional element 102, one or both of the first segment 130 and the second segment 132 of the attachment portion 110 can extend into the space 146 located between the arms 140 of the retention portion 138.

In some embodiments, the retention portion 138 can have a length sufficient to permit, or facilitate, deformation of a portion of the manipulation member 104 into the region 146. In some embodiments, the retention portion 138 can extend proximally a distance sufficient to allow manipulation of the retention portion 138 while the interventional element 102 is positioned within the cerebral vasculature and the retention portion 138 extends through an access catheter. In some embodiments, the retention portion 138 can extend proximally indefinitely.

Figure 5:
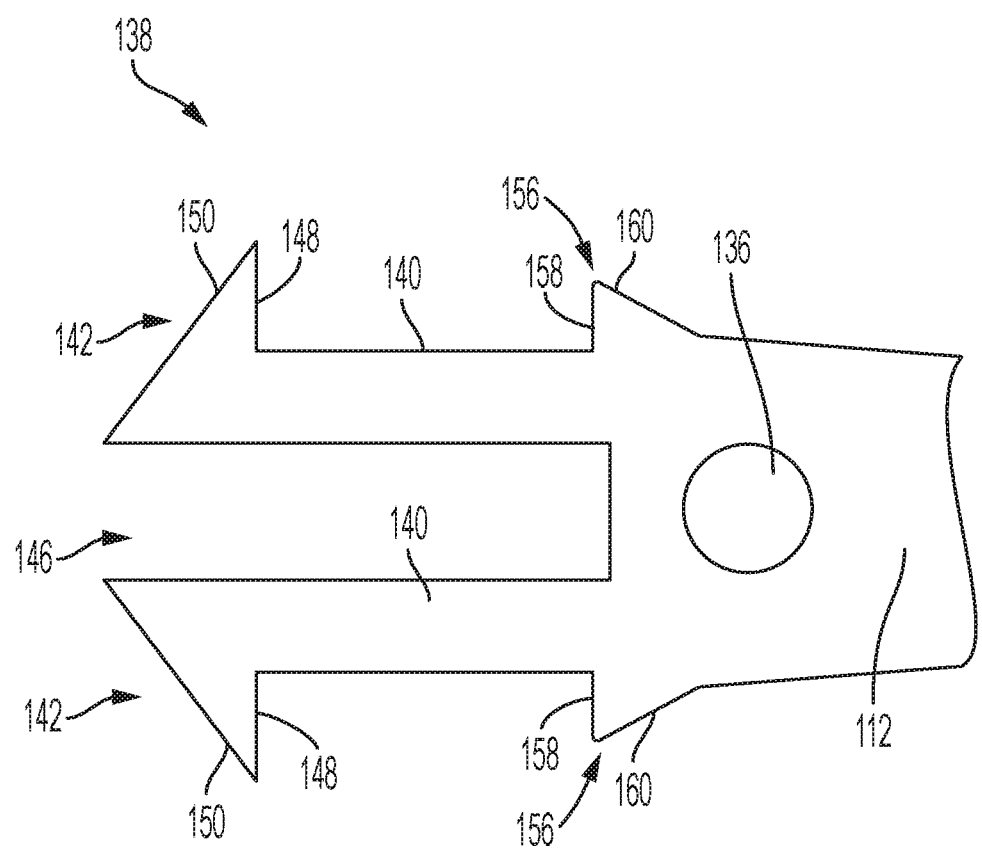
FIG. 5 illustrates an enlarged view of a proximal portion of an interventional element according to some embodiments.
Figure 6A:
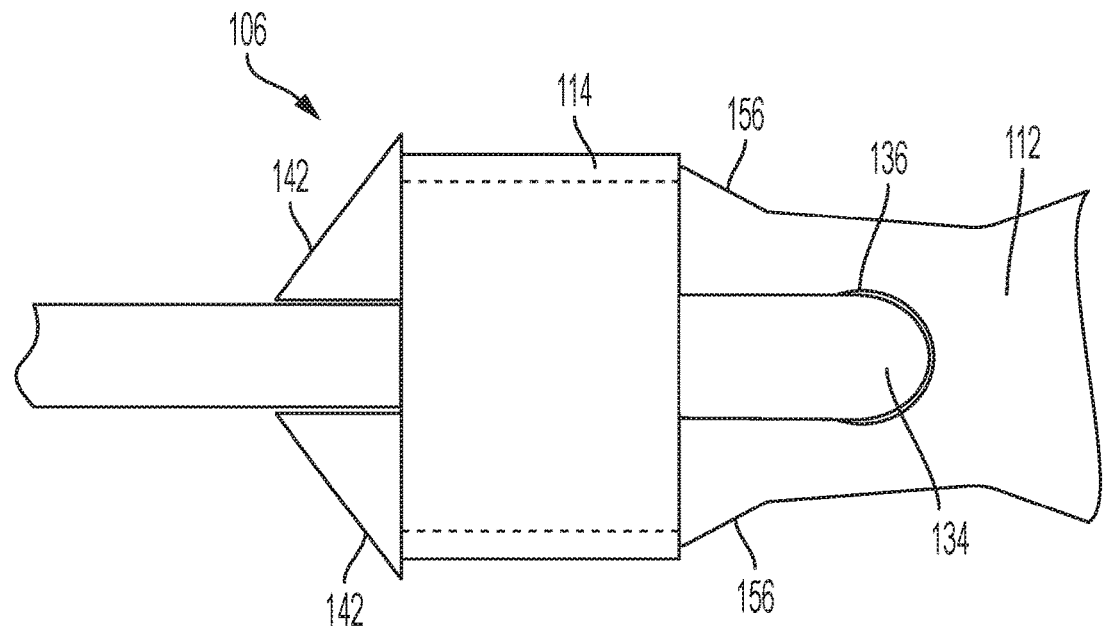
FIG. 6A is a schematic top view of a connection between a manipulation member and an interventional element according to some embodiments.
Figure 6B:
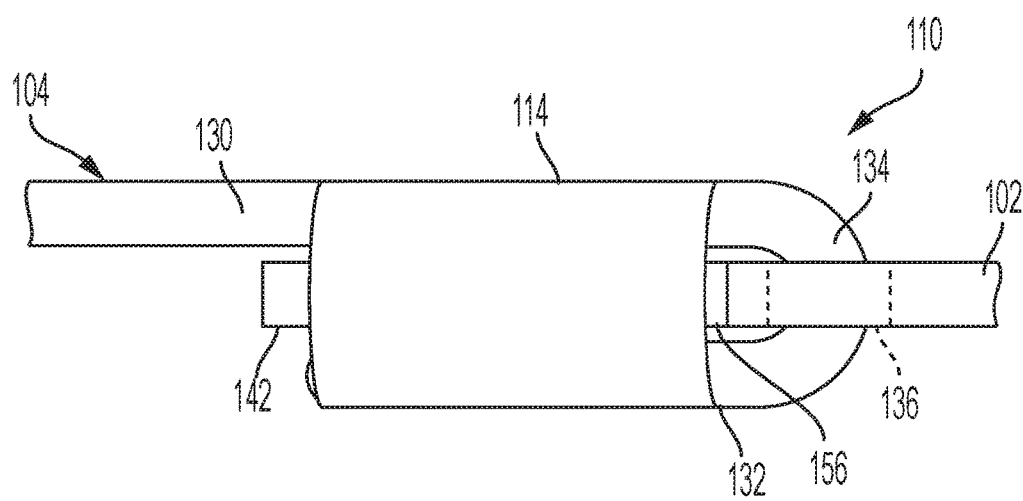
FIG. 6B is a schematic side view of the connection shown in FIG. 6A.
Figure 7:
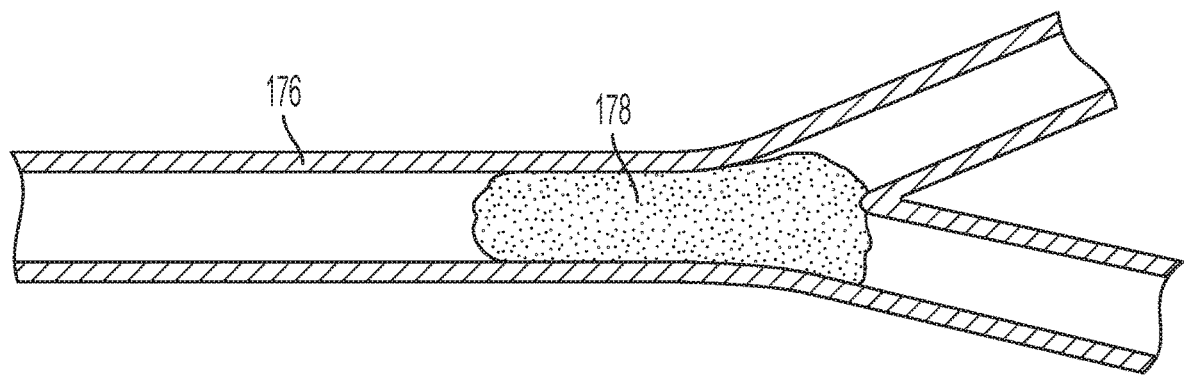
FIGS. 7-11 are schematic illustrations of method steps for performing an exemplifying intravascular procedure of restoring blood flow in an obstructed blood vessel using the device for intravascular intervention of FIG. 1A.
Figure 8:
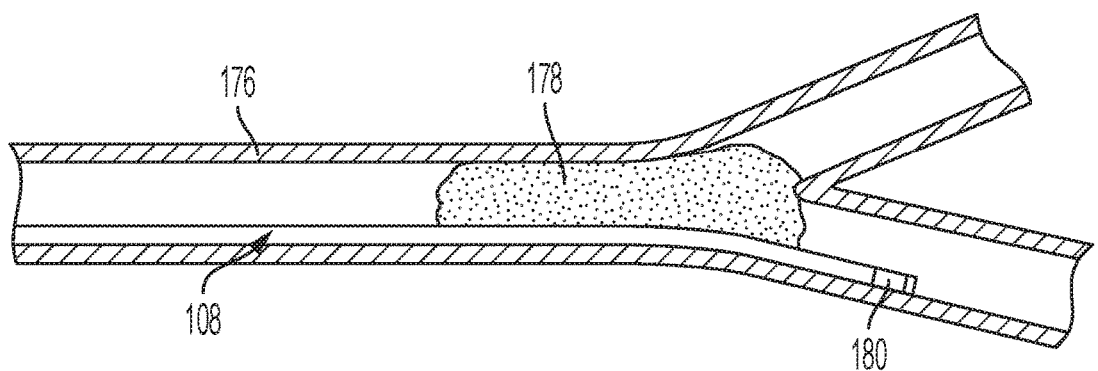

FIG. 5 illustrates another embodiment of a retention portion 138 of an interventional element 102. FIGS. 6A and 6B illustrate top and side views, respectively, of a connection 106 using the retention portion 138 shown in FIG. 5. In the illustrated embodiment, the retention portion 138 includes distal engagement members 156 in addition to the proximal engagement members 142 as in the embodiment shown in FIGS. 4A-4C. As illustrated in FIG. 5, each arm 140 can include a distal engagement member 156, which can take the form of a shoulder, barb, ridge, bump, protrusion, or other suitable structural feature configured to engage the joining element 114. In the illustrated embodiment, the distal engagement members 156 each include a proximal-facing surface 158 and a distal-facing surface 160. The proximal-facing surface 158 can take the form of a flange, shoulder, or other engagement surface configured to abut the distal end face 154 of the joining element 114. The distal-facing surfaces 160 can be sloped, for example being sloped radially inwardly in the distal direction. In other embodiments, the distal-facing surfaces 160 can assume other shapes or configurations. In operation, the proximal-facing surfaces 158 can abut the joining element 114 to limit distal movement of the interventional element 102 with respect to the joining element 114.

As noted above, the connection 106 can comprise a joining element 114 in the form of a band, collar, coil, etc. in some embodiments. For example, a circumferential band can hold the attachment portion 110 against the retention portion 138 and/or otherwise maintain the portions 110, 138 in an interlocked relationship. Additionally or alternatively, the band can serve as a radiopaque marker. In some embodiments, the band can hinder separation of the attachment portion 110 from the retention portion 138. In some embodiments, the band can be slid or crimped onto one or both of the attachment portion 110 and the retention portion 138. In some embodiments, the band can be slid or crimped onto each of the attachment portion 110 and the retention portion 138. In embodiments wherein band serves as a radiopaque marker, sliding or crimping the band directly to the retention portion 138 can retain the marker band on the retention portion 138 in the unlikely event of unintentional separation of the manipulation member 104 from the interventional element 102.

The joining element 114 can surround all or a portion of the length of the attachment portion 110, the retention portion 138, or both in the device 100. In some embodiments, the joining element 114 does not extend over at least a part of the proximal portion 112 of the interventional element 102. For example, in some embodiments, the joining element 114 does not surround a part, of the proximal portion 112, that surrounds the opening 136.

The joining element 114 can be a sleeve that is circumferentially continuous. Alternatively, the joining element 114 can be circumferentially discontinuous and can have lateral edges that overlap when the band is attached at the connection 106. In some embodiments, a clip that only partially surrounds all or a portion of the length of the attachment portion 110, the retention portion 138, or both in the device 100 can be used in addition or alternative to the joining element 114. In some embodiments, the joining element completely or substantially surrounds at least a section of the attachment portion 110 and a segment of the retention portion 138.

In embodiments wherein the joining element serves as a marker, the joining element can be formed of a radiopaque material such as, for example, platinum or platinum alloys, including platinum-iridium. In some embodiments, the joining element can be formed of a non-radiopaque material.

The joining element 114 can have a maximum cross-sectional (lateral) dimension that is 0.027 inch or less, 0.021 inch or less, or 0.015 inch or less, in some embodiments. The joining element 114 can have cross-sectional dimension(s) that inhibit or prevent movement of the joining element distally over the proximal portion 112 of the interventional element 102. For example, the cross-sectional dimension can be a diameter (inner or outer) that is less than a width of the proximal portion 112.

In some embodiments, the connection 106 can comprise a bonding agent in addition or alternative to the band in some embodiments. The bonding agent can strengthen the connection 106 between the interventional element 102 to the manipulation member 104, and/or hinder separation of the attachment portion 110 from the retention portion 138. The bonding agent can bond to each of the attachment portion 110 and the retention portion 138. The bonding agent can comprise adhesive, solder, welding flux, brazing filler, etc. In some embodiments, the bonding agent can bond to the attachment portion 110 in the retention portion 138 without applying heat. For example, the bonding agent can comprise a UV-curable adhesive. In embodiments that comprise a polymer coating of the wire or polymer tubing, use of a bonding agent that avoids application of heat that would damage the polymer may be preferred.

In some embodiments, the bonding agent can cover the bend 134 of the attachment portion 110, a proximal end of the connection 106, or both. In embodiments that comprise a band and a bonding agent, the bonding agent can fill all or a portion of an interior volume of the band in addition or alternative to covering one or both ends of the connection 106. By covering one or both ends of the connection 106, the bonding agent can form rounded, atraumatic end surface(s) that cover any relatively sharp ends of the components that form the connection 106. In some embodiments, the manipulation member 104 tapers at an intersection with the bonding agent. Tapering of the wire at the intersection with the bonding agent can concentrate stress at the intersection to promote breakage at the intersection in the event that the manipulation member 104 breaks, thereby retaining the joining element 114 on the interventional element 102. Retention of the band on the interventional element may be desirable in embodiments wherein band serves as a marker.

In some embodiments, the manipulation member 104 can be attached to the interventional element 102 at the connection 106 by the processes described below and variants thereof. The attachment portion 110 of the manipulation member 104 can be positioned about a part of the proximal portion 112 of the interventional element 102. For example, a distal end portion of the manipulation member 104 can be passed through the opening 136. The attachment portion 110 of the manipulation member 104 can extend through the opening 136 at the bend 134 such that the first segment 130 and the second segment 132 are on different sides of the proximal portion 112 of the interventional element 102. In some embodiments, the terminal distal end of the manipulation member 104 can be located proximally of the bend 134. In some embodiments, the manipulation member 104 can be bent to interlock with the proximal portion 112 of the interventional element 102.

In some embodiments wherein the manipulation member 104 comprises a plurality of components, the components of the manipulation member can be assembled together prior to attachment of the manipulation member to the interventional element 102. For example, in some embodiments, a wire, a coil, and one or more tubes can be assembled together, before a portion of the wire is passed through the opening 136 in the proximal portion 112 of the interventional element 102, before the wire is bent, or both.

The manipulation member 104 can be bent in one or more stages between an initial straight configuration and a final configuration in the completed device 100. For example, the manipulation member 104 can be bent by an initial amount before any portion of the manipulation member 104 is passed through the opening 136 and bent a further amount thereafter. The manipulation member 104 can be initially bent between 10° and 170°, between 45° and 160°, between 90° and 145°, or between 125° and 135°, from a straight configuration, prior to any portion thereof being passed through the opening 136. After segment of the manipulation member 104 has been passed through the opening 136, the manipulation member 104 can be bent by a further amount to accommodate the joining element 114, if present. In some embodiments, the manipulation member 104 can be finally bent to between 150° and 210°, between 160° in 200°, or between 170° and 190°. Preferably, the final bend 134 has no substantial surface crack.

If the joining element 114 cannot be positioned over the attachment portion 110 without further deflection of the manipulation member 104, the manipulation member 104 can be bent, or further bent, to accommodate the joining element 114. In some embodiments, the joining element 114 can be positioned over the manipulation member 104 or the interventional element 102 prior to coupling the manipulation member and the interventional element. The joining element 114 can be positioned around all or a portion of the attachment portion 110 and all or a portion of the retention portion 138 by moving the band a proximal or distal direction. In some embodiments, the joining element 114 is moved over the manipulation member 104 in a distal direction and, as the joining element 114 is advanced onto the attachment portion 110, a terminal distal end of the wire can be deflected to enter an interior of the joining element 114. Then, the manipulation member can be further bent as the joining element 114 is advanced farther distally, and optionally with the terminal distal end of the manipulation member 104 being held stationary.

In embodiments that comprise a bonding agent, the bonding agent (not shown) can be applied to the attachment portion 110 of the manipulation member 104 and the retention portion 138 of the interventional element 102 after a segment of the manipulation member has been positioned about the proximal portion 112. If the connection 106 comprises a band and bonding agent, the bonding agent can be applied at the connection 106 before or after the band is attached at the connection 106. If the terminal distal end of the manipulation member 104 extends proximally beyond a proximal end of the band, the manipulation member 104 can be trimmed so that the terminal distal end of the wire is approximately even with the proximal end of the band before applying the bonding agent.

Although some embodiments comprise both a band and a bonding agent, some embodiments comprise a band without a bonding agent, and some embodiments comprise a bonding agent without a band. Some embodiments can omit both a band and a bonding agent. For example, a manipulation member 104 and an interventional element 102 can be integrally formed in some embodiments. For another example, a manipulation member 104 separately formed from an interventional element 102 can be attached to the interventional element without use of a band or bonding agent.

Various methods are available for bending the manipulation member 104 prior to attachment to the interventional element 102. For example, the manipulation member 104 can be bent around a fixed mandrel. However, bending the wire around a fixed mandrel may yield inconsistent results and may damage wire by introducing surface cracks that reduce the tensile strength of the manipulation member 104. Likewise, manual bending of the wire may likewise yield inconsistent results and may damage the manipulation member 104 by introducing substantial surface cracks. For another example, a bend in the manipulation member 104 and may be heat set. However, heat setting may require more time than other bending methods and may adversely affect other portions of the manipulation member 104. For example, if the manipulation member includes tubes comprising polymers or other heat sensitive materials, heat setting may damage those portions of the manipulation member 104. These and other methods may be used to bend manipulation member 104 comprising stainless steel, nickel titanium alloys, or other metals.

The connection 106 can substantially permanently couple the interventional element 102 and manipulation member 104 during use of the device 100 for intravascular intervention. For example, the connection 106 can couple the interventional element manipulation member during insertion of the interventional element into a blood vessel, e.g., a cerebral blood vessel, using the manipulation member, manipulation of the interventional element to perform a therapy within the blood vessel, and removal of the interventional element from the blood vessel using the manipulation member. In some embodiments, the device 100 can be inserted through a microcatheter. The interventional element can be removed from the blood vessel in some embodiments by proximally pulling the manipulation member 104, for example to retract the interventional element into a microcatheter. The interventional element can be deployed in some embodiments by maintaining a location of the interventional element while retracting the microcatheter from over the interventional element.

II. Example Methods of Use

With reference to FIGS. 7-11, the device 100, including the manipulation member 104 and interventional element 102, can be used as a flow restoration device. For example, the interventional element can comprise a self-expanding member used to restore blood flow in a medical patient experiencing ischemic stroke due to large intracranial vessel occlusion. In a preferred arrangement, the device 100 can be used in conjunction with a microcatheter 108. The device 100 can retrieve thrombi from highly tortuous, small, and thin wall vessels. The device 100 can be used to treat vessels with diameters, for example, ranging from 2.0 mm to 5.5 mm, such as the internal carotid artery, M1 and M2 segments of the middle cerebral artery, anterior cerebral artery, basilar artery and vertebral artery, though other ranges, sizes, and particular vessels are also possible.

During a flow restoration procedure, a balloon guide catheter (not shown) can be moved through the vasculature towards a treatment area. A balloon, located on a distal end of the balloon guide catheter, can be expanded against the walls of a blood vessel 176. The microcatheter 108 can first be delivered through the balloon guide catheter. The interventional element 102 can then be delivered through the microcatheter 108. Alternatively, the interventional element 102 can be delivered with the microcatheter 108. The interventional element 102 can be in a volume-reduced form within the microcatheter 108. The microcatheter 108 can be advanced through the vessel 176 and placed adjacent a thrombus 178. The interventional element 102 can be positioned such that the connection 106 is upstream of the thrombus 178, a distal end of the interventional element is downstream of the thrombus, and a portion of the interventional element 102 is located radially adjacent to the thrombus 178. In a preferred arrangement illustrated in FIG. 8, the microcatheter 108 can be placed alongside the thrombus 178 such that a distal tip 180 of the microcatheter 108 is beyond the thrombus 178, wherein the distal tip 180 is from greater than about 0 mm to about 10 mm or more, or about 3 mm to about 5 mm beyond the thrombus 178, though other ranges and values are also possible. In a preferred arrangement, the interventional element 102 can be positioned such that portions of the interventional element 102 extend both proximally and distally of thrombus 178.

Figure 9:
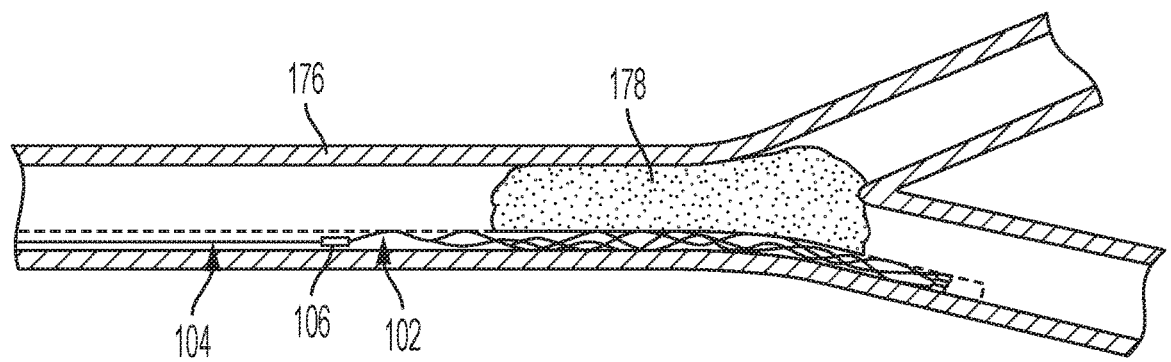

As illustrated in FIG. 9, the interventional element 102 can be held in a fixed position by holding the manipulation member 104 stationary while the microcatheter 108 is withdrawn (i.e., pulled proximally). As the microcatheter is withdrawn, the interventional element 102 can be released from its volume-reduced form, and can expand. The interventional element 102 can assume at least a portion of its unconstrained form, thereby expanding to bring at least part of the interventional element 102 into penetrating contact with the thrombus 178. If the position of the interventional element 102 needs to be adjusted, the manipulation member 104 and/or microcatheter 108 can be moved together or individually, and if necessary, the interventional element 102 can be placed back in the microcatheter and then expanded again, or redeployed.

Once deployed, the interventional element 102 can exert an outward radial force on the thrombus 178, as described above, thus reducing the cross-sectional area of the thrombus 178, forming a channel for immediately re-establishing at least partial blood flow through the blood vessel 176 past the thrombus 178, and/or loosening the thrombus from the vessel wall. In some embodiments, for example, about 10% to about 60% of the original thrombus 178 circumference can be separated from the vessel wall after the interventional element 102 is deployed, and the ability of the thrombus 178 to hang onto the vessel wall via adhesion and friction can accordingly be reduced. In some embodiments, the cross sectional area of the thrombus 178 can be significantly reduced by the deployed interventional element 102, resulting in a thrombus 178 having about 30% to about 95% of its original cross sectional area, but more typically about 50% to about 80% of its original cross-sectional area. In some embodiments, administration of an effective amount of a clot-busting drug, such as, for example tissue plasminogen activator (tPA), to the site of the thrombus 178 can further be applied during the blood flow restoration procedure to enhance dissolution of the thrombus 178. In some embodiments, the open channel created by the interventional element 102 can increase the exposed surface area of the thrombus 178, thereby facilitating faster dissolution of the thrombus 178 with such clot-busting drugs.

Figure 10:
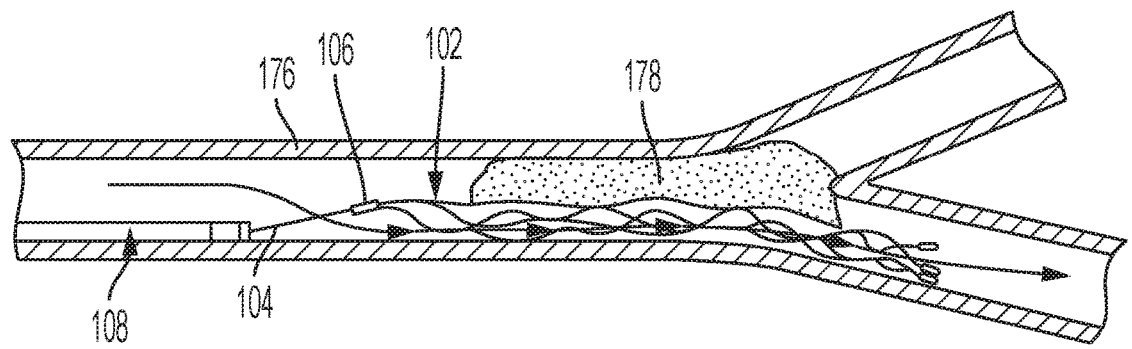
Figure 11:
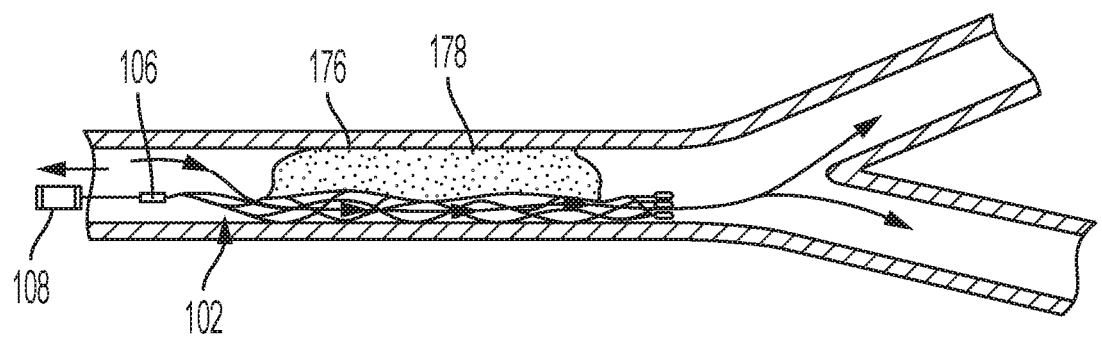

With reference to FIGS. 10 and 11, once the interventional element 102 has engaged and captured the thrombus 178, the thrombus 178 can be removed. Prior to pulling back on the manipulation member 104, the microcatheter 108 can be manipulated. For example, the microcatheter 108 can be moved forward to a predetermined point relative to the interventional element 102. Use of markers along the microcatheter 108 and/or interventional element 102 can be used to determine the relative locations of the microcatheter 108 and interventional element 102. For example, the microcatheter 108 can be moved distally until it covers the joining element 114. The microcatheter 108 and interventional element 102 can then be removed together.

With reference to FIG. 11, during retrieval of the device 100 and thrombus 178, the initial channel created for flow restoration through or past the thrombus 178 can remain open. The balloon can remain inflated to provide for maximum proximal flow control. For example, in some embodiments the balloon can ensure that there is no flow proximally through the vessel from the balloon towards the interventional element 102. As part of the retrieval procedure, continuous aspiration can be employed through the balloon guide catheter with vigorous aspiration when the interventional element 102 is near a distal tip of the balloon guide catheter. Aspiration assistance can enable flow reversal through the interventional element 102 and thrombus 178. The aspiration with flow reversal can help allow the distal vasculature to continue to have blood perfusion through the vessels during the retrieval process and can inhibit the possibility of distal emboli. There can be an advantage to having blood flow across the self-expanding device 102 and thrombus 178 with the potential of natural lysing of blood and increased surface area for thrombus dissolving medicines, if they are provided. The aspiration with flow reversal can also assist in the thrombus retrieval process by aiding in the removal of the thrombus 178. The flow can be directed towards the lumen of the balloon guide catheter due to the aspiration. The interventional element 102 and thrombus 178 can thus be assisted by the flow to enter the lumen of the balloon guide catheter. In some embodiments, if withdrawal into the balloon guide catheter is difficult for any reason during aspiration, the balloon can be deflated, and the balloon guide catheter, microcatheter 108, and the device 100 can be withdrawn simultaneously as a unit while maintaining aspiration.

In some embodiments, device 100 can be used as a device for use as an implantable member (e.g., stent). For example, the manipulation member 104 and interventional element 102, coupled at the connection 106, can be delivered through a microcatheter 108 to a treatment site such as a stenosis or aneurysm. Similar to the method described above, the microcatheter can be withdrawn, and the interventional element 102 can expand against a vessel wall. Similar to use as a flow restoration device, if necessary, the interventional element 102 can be repositioned if it is not placed correctly on a first attempt. Once the interventional element 102 is in a desired location at the treatment site, the interventional element 102 can then be detached from the manipulation member 104 and be used as an implantable member.

III. CONCLUSION

This disclosure is not intended to be exhaustive or to limit the present technology to the precise forms disclosed herein.

Although specific embodiments are disclosed herein for illustrative purposes, various equivalent modifications are possible without deviating from the present technology, as those of ordinary skill in the relevant art will recognize. In some cases, well-known structures and functions have not been shown and/or described in detail to avoid unnecessarily obscuring the description of the embodiments of the present technology. Although steps of methods may be presented herein in a particular order, in alternative embodiments the steps may have another suitable order. Similarly, certain aspects of the present technology disclosed in the context of particular embodiments can be combined or eliminated in other embodiments. Furthermore, while advantages associated with certain embodiments may have been disclosed in the context of those embodiments, other embodiments can also exhibit such advantages, and not all embodiments need necessarily exhibit such advantages or other advantages disclosed herein to fall within the scope of the present technology. Accordingly, this disclosure and associated technology can encompass other embodiments not expressly shown and/or described herein.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like are used throughout this disclosure to mean including at least the recited feature(s) such that any greater number of the same feature(s) and/or one or more additional types of features are not precluded. Directional terms, such as "upper," "lower," "front," "back," "vertical," and "horizontal," may be used herein to express and clarify the relationship between various elements. It should be understood that such terms do not denote absolute orientation. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

The invention claimed is:

1. A device for intravascular intervention, the device comprising:
    an elongate manipulation member comprising a distally located attachment portion, the attachment portion comprising a first segment, a second segment, and a bend between the first and second segments;
    an interventional element comprising:
        a proximal end portion including a hole, the attachment portion of the elongate manipulation member extending through the hole at the bend such that the first and second segments each extend proximally from the hole; and
        a retention portion comprising an arm extending proximally of the hole and a shoulder protruding radially outwardly from a proximal portion of the arm, wherein the shoulder comprises a substantially planar distal-facing surface and an angled proximal-facing surface; and
    a joining element configured to circumferentially surround at least a portion of the retention portion and at least a portion of the first and second segments of the elongate member such that a proximal end of the joining element is positioned distal to the shoulder of the retention portion, wherein the proximal end of the joining element is configured to engage the distal-facing surface of the shoulder.

2. The device of claim 1, wherein the arm is a first arm and the shoulder is a first shoulder, the retention portion further comprising:
    a second arm extending proximally of the hole; and
    a second shoulder protruding radially outwardly from a proximal portion of the second arm,
    wherein the joining element is configured to circumferentially surround at least a portion of the retention portion such that the proximal end of the joining element is positioned distal to the second shoulder of the retention portion.

3. The device of claim 2, further comprising a longitudinal axis intersecting the hole, wherein the first arm extends away from the longitudinal axis in a first direction, and wherein the second arm extends away from the longitudinal axis in a second direction opposite the first direction.

4. The device of claim 2, further comprising a third shoulder protruding radially outwardly from the first arm at a position distal to the first shoulder; and a fourth shoulder protruding radially outwardly from the second arm at a position distal to the second shoulder.

5. The device of claim 4, wherein the third shoulder and the fourth shoulder are configured to engage a distal end of the joining element.

6. The device of claim 1, wherein the joining element comprises a cylindrical band.

7. The device of claim 1, wherein each of the first and second segments of the elongate manipulation member extends proximally of the joining element.

8. The device of claim 1, wherein the arm is radially outwardly biased, and wherein the joining element is configured to retain the arm in a displaced state.

9. The device of claim 1, wherein the shoulder protrudes laterally to an extent, measured from the arm, by an amount that is greater than or equal to a wall thickness of the joining element.

10. The device of claim 1, wherein:
    the proximal end portion of the interventional element has a top side and a bottom side;
    the hole extends through the proximal end portion between the top side and the bottom side; and
    at least one of the first segment or the second segment of the elongate manipulation member has an extending portion that extends into a region that is (i) between the top side and the bottom side of the proximal end portion, and (ii) between the shoulder of the retention portion and the hole.

11. A device for intravascular intervention, the device comprising:
    a band having a lumen;
    an elongate manipulation member having a distally located attachment portion, the elongate manipulation member extending through the lumen; and
    an interventional element comprising:
        a proximal end portion including a hole, the attachment portion of the elongate manipulation member extending through the hole; and
        a plurality of projections extending proximally of the hole and through the lumen, at least one of the projections including a flange extending laterally away from a longitudinal axis of the device and configured to engage with the band, wherein the flange limits distal movement of the interventional element with respect to the band.

12. The device of claim 11, wherein the flange is configured to abut a proximal end portion of the band.

13. The device of claim 11, wherein the at least one projection comprises a proximally facing surface opposite the flange, the proximally facing surface being sloped in a proximal direction towards a central longitudinal axis of the device.

14. The device of claim 11, wherein the plurality of projections are biased laterally outwardly from a central longitudinal axis of the device.

15. A device for intravascular intervention, the device comprising:
- an elongate manipulation member comprising a distally located attachment portion;
- an interventional element comprising:
  - a proximal end portion including a hole, the attachment portion of the elongate manipulation member extending through the hole; and
  - a plurality of arms extending proximally of the hole and extending laterally outwardly from a longitudinal axis of the device, each of the arms having a protrusion thereon having a proximal-facing surface and a distal-facing surface; and
- a joining element circumferentially surrounding the arms such that each of the distal-facing surfaces of the protrusions abuts a proximal-facing engagement surface of the joining element.

16. The device of claim 15, wherein the proximal-facing engagement surface of the joining element comprises a proximal end face of the joining element.

17. The device of claim 15, wherein the distal-facing surfaces of the protrusions are sloped laterally inwardly in a proximal direction.

18. The device of claim 15, wherein a portion of the elongate manipulation member extends laterally between the arms.

19. The device of claim 15, wherein the distal-facing surface of the protrusion of each of the arms is substantially planar, and the proximal-facing surface of the protrusion of each of the arms is angled.

20. The device of claim 15, wherein the protrusion of each of the arms limits distal movement of the interventional element with respect to the joining element.

* * * * *

UNITED STATES PATENT AND TRADEMARK OFFICE
CERTIFICATE OF CORRECTION

| | |
|---|---|
| PATENT NO. | : 11,738,188 B2 |
| APPLICATION NO. | : 16/946146 |
| DATED | : August 29, 2023 |
| INVENTOR(S) | : Skillrud et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 632 days.

Signed and Sealed this
Twelfth Day of November, 2024

Katherine Kelly Vidal
*Director of the United States Patent and Trademark Office*